United States Patent [19]
Ryan

[11] Patent Number: 5,139,483
[45] Date of Patent: Aug. 18, 1992

[54] MEDICAL INTRAVENOUS ADMINISTRATION LINE CONNECTOR

[75] Inventor: Dana W. Ryan, Franklin, Tenn.

[73] Assignee: Ryan Medical, Inc., Brentwood, Tenn.

[21] Appl. No.: 807,409

[22] Filed: Dec. 12, 1991

Related U.S. Application Data

[63] Continuation of Ser. No. 520,022, May 7, 1990, abandoned.

[51] Int. Cl.⁵ .............................................. A61M 25/00
[52] U.S. Cl. ..................................... 604/86; 604/283; 604/905
[58] Field of Search ................................. 604/86–88, 604/201, 206, 240, 243, 244, 283, 411, 414, 905

[56] References Cited

U.S. PATENT DOCUMENTS

| | | | |
|---|---|---|---|
| 3,986,508 | 10/1976 | Barrington | 604/283 |
| 4,511,359 | 4/1985 | Vaillancourt | 604/411 |
| 4,559,043 | 12/1985 | Whitehouse et al. | 604/243 |
| 4,752,292 | 6/1988 | Lopez et al. | 604/905 |
| 4,946,445 | 8/1990 | Lynn | 604/905 |
| 4,950,260 | 8/1990 | Bonaldo | 604/905 |
| 4,981,469 | 1/1991 | Whitehouse et al. | 604/86 |

FOREIGN PATENT DOCUMENTS 0157224 10/1985 European Pat. Off. ............ 604/905

*Primary Examiner*—John D. Yasko
*Assistant Examiner*—Anthony Gutowski
*Attorney, Agent, or Firm*—David P. Gordon

[57] ABSTRACT

An IV quick-connect/disconnect device is provided and generally comprises suitably molded single piece male and female connectors. The male connector has a male luer-lock on one end, one or more outwardly extending bayonet knobs on a middle portion and a reduced diameter second end which terminates in a resilient septum. The female connector has a female luer-lock on one end and a receiving cylinder with a bayonet cut out on the other; the luer-lock and the cylinder being separated by a wall through which a hollow needle extends that has been insert molded in the wall. The male and female connectors are mated by sliding the reduced diameter second end of the male connector into the receiving cylinder of the female connector, with the bayonet cutouts of the female connector serving as a track for the extended knobs of the male connector. The connectors are locked into place by bringing the male connector as far forward as possible, and then rotating the male connector such that extending knobs move past the restriction in the cutout and click (lock) into place.

13 Claims, 3 Drawing Sheets

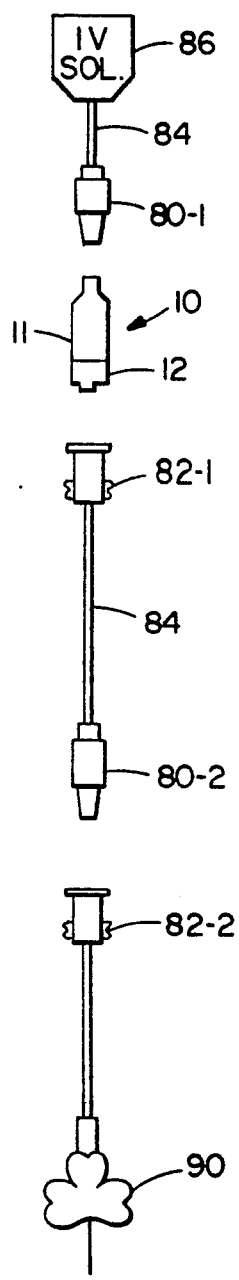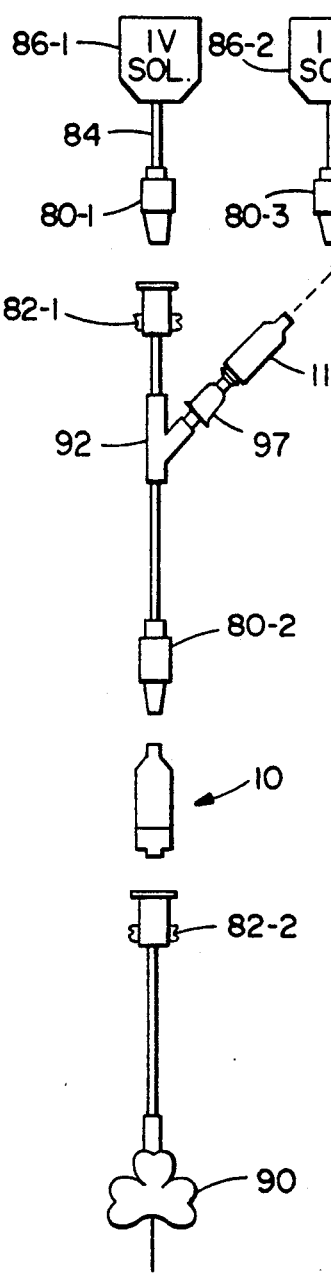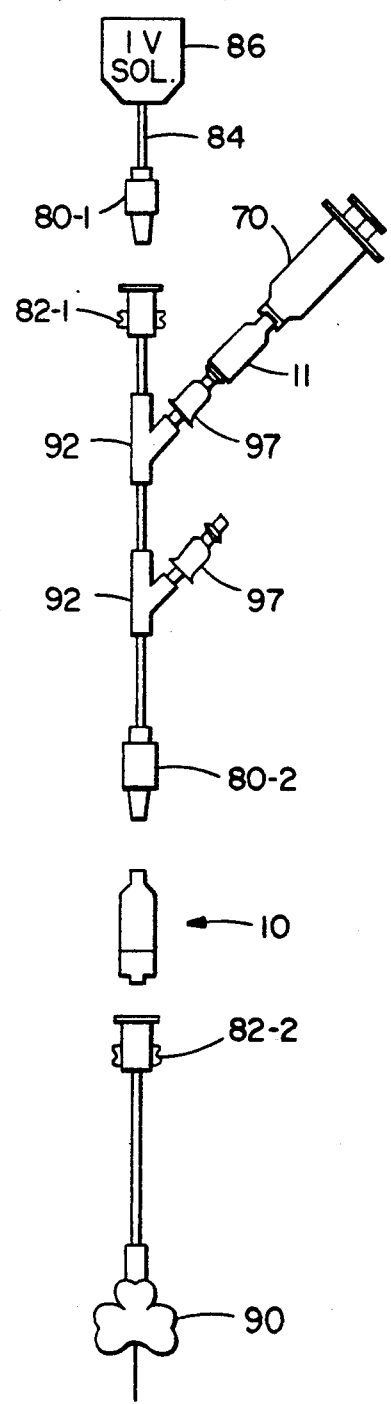

MEDICAL INTRAVENOUS ADMINISTRATION LINE CONNECTOR

This is a continuation of co-pending application Ser. No. 07/520,022 filed on May 7, 1990 (now abandoned).

BACKGROUND OF THE INVENTION

This invention relates to connectors for use with intravenous administration lines and systems in the medical field, and more particularly relates to a two part IV quick-connect/disconnect safety assembly that makes it more convenient to attach and detach a patient to and from an IV system.

Intravenous therapy has a long history of use in supplying patients with medicament, nourishment or fluids. One of the problems associated with intravenous therapy of ambulatory patients is that the patient cannot be easily disconnected from and reconnected to an intravenous administration line for short periods of time. To safely and easily disconnect the patient for even a short period of time requires the assistance of skilled medical personnel. The ambulatory patient is often required to be attached to the intravenous system and must wheel a stand holding the IV liquid supply wherever the patient goes. Being restricted in this manner can cause the patient to forgo activities of short duration that would be beneficial to the patient.

It is often necessary for hospital staff to move patients from location to location within the hospital in order to perform tests and certain medical treatments. It is not necessary or desirable to have the patient hooked up to the intravenous system during some of these activities. Removing a patient from an intravenous system and re-establishing the patient on the system takes a substantial amount of time even for a medical professional skilled in the techniques of intravenous therapy. With hospital costs rising dramatically there is considerable advantage in a connector device that allows the medical staff to be able to quickly and safely connect and disconnect a patient from an intravenous therapy administration line while expending a minimum amount of time in doing so.

The prior art has addressed some of the above stated problems. For example, U.S. Pat. No. 4,511,359 issued to Vaillancourt describes a three-part sterile dialysis connection device for home use. The three parts are a male connector which terminates in a catheter tube; a female connector with a hollow needle secured in place and terminating in a flexible tubing; and a molded septum assembly. Vaillancourt places the molded septum assembly in the receiver end of the female connector. The female connector is then slid over the male connector, thereby pushing the septum assembly into place between the male and female connectors, and into friction fit with the male connector, and also causing the sharpened needle in the female connector to pierce the molded septum assembly. The hollow needle provides a path for fluid flow between the two connector parts. When the male and female connectors are separated, the needle is removed from the self-sealing septum, and the septum assembly remains with and covering the male connector because of its friction fit therewith.

Another three-part home dialysis connection device is described in U.S. Pat. No. 4,810,241 issued to Rogers which provides a sterile connection by mechanical and chemical means. The three parts include two connectors, one attached to an influent tube and the other to the catheter tube, and a cylindrical shaped tube in which there is highly absorbent material saturated with antiseptic. The two connectors in turn connect one to each end of the cylinder. As the end connectors are introduced into the central cylinder connector, they are sterilized by the antiseptic in the cylinder and remain in antiseptic contact during the entire time they are being used for dialysis. A sterile environment is maintained on the catheter tubing side of the IV system only for so long as the catheter side tubing is in the connector cylinder. Care must be taken not to let the disinfectant in the cylinder dry out or evaporate.

A somewhat different solution to the problem was taken by U.S. Pat. No. 4,559,043 issued to Whitehouse, et al. which provides a four-piece assembly including a distal connector, a proximate connector, a septum fitting between and held in place by the distal and proximate connectors, and an adapter with a through bore able to accept a hollow needle, the adapter being used in conjunction with the proximate connector. A hollow needle attached to a standard luer extension T which connects to the adapter is pushed through the adapter needle bore and pierces the septum which is held between the proximate and distal connectors, thereby establishing fluid flow. When the hollow needle attached to the luer T is removed, the septum is sealed, but the needle is exposed, presenting a needlestick hazard.

The prior art of FIG. 1 shows a connector 100 manufactured by ICU Medical Inc., Irvine, Calif. and illustrates the extreme complexity some IV line connectors have embodied in an attempt to solve the problems in the art. The prior art connector 100 has a female portion 110 and a male portion 103. A spring loaded thumb lever 112 which protrudes from the side of the female connector 110 is provided to clamp a rear flange 124 of the male connector 103 against the end surface 117 of the female connector 110. The plastic spring 109 shown in FIG. 1 provides the spring action which holds the lever 112 in the locked position The connector is complex and difficult to manufacture, expensive to make, and potentially hazardous due to the high probability of the lever 112 becoming caught on bed rails, medical equipment, or tubing at a patient's bedside.

While the devices of the prior art may be effective for their particular purposes, the requirement for a simple, low-cost, quick-connect/disconnect safety assembly is not filled. The prior art does not show a device which has all of the virtues in a single device of being simple and inexpensive to manufacture, providing standard means such as luer fittings for attachment to other devices, and providing means for shielding the needle after use to prevent accidental needlesticks.

SUMMARY OF THE INVENTION

It is therefore an object of the invention to provide a simple, low cost, IV quick-connect/disconnect safety assembly.

Another object is to provide an IV quick-connect/disconnect assembly that is streamlined and has no projections or protruding parts which might catch or snag.

A further object of the invention is to provide an IV quick-connect/disconnect assembly designed so that the needle piercing the septum of the male connector is contained in a shielded area at all times, thereby substantially minimizing the probability of accidental needlesticks.

Another object of the invention is to provide an IV quick-connect/disconnect assembly that will reduce the average time it takes medical personnel to establish the IV therapy system servicing a patient.

Yet another object of the invention is to provide an IV quick-connect/disconnect assembly that has means at both ends that permit attachment to any type of standard administration lines, extension sets, winged needles, catheters, or other IV medical devices using standard medical attachment means such as luer-locks or luer-slip fittings.

An even further object is to use the female portion of the quick-connect/disconnect assembly in conjunction with a syringe device to provide a safety syringe with may be used for injection into an IV administration line or PRN device.

In accordance with the objects stated above an IV quick-connect/disconnect assembly is provided and generally comprises suitably molded single piece male and female connectors. The male connector has a male luer-lock on one end, one or more outwardly extending knobs on a middle section of slightly reduced diameter and a further reduced diameter second end which is enclosed by a resilient molded septum or the like. The female connector has a female luer-lock on one end and a receiving cylinder on the other, the luer-lock and the cylinder being separated by a wall through which a hollow needle extends that has been insert molded or bonded in the wall. The pointed end of the hollow needle is located in the receiving cylinder. The receiving cylinder has one or more bayonet cutouts in its outer surface which are arranged to receive the outwardly extending knobs of the male connector when the reduced diameter second end of the male connector is placed in the receiving cylinder of the female connector. When mated, the top of the knobs are flush with the outside cylindrical surface of the female connector, and the surfaces of the male and female connectors form a smooth streamlined surface with no projections that can catch or snag other medical equipment.

In using the male and female connectors, an IV administration line with a male luer-lock or luer-slip is inserted into the female luer side of the female connector, while an IV winged needle or catheter device that is connected directly to an extension line or the like which terminates in a female luer-lock or luer-slip is connected with the male luer-lock or luer-slip of the male connector. The male and female connectors are mated by sliding the reduced diameter second end of the male connector into the receiving cylinder of the female connector, with the cutouts of the female connector serving as a track for the extended knobs of the male connector. As the male connector is slid forward, the needle in the female connector pierces the resilient septum which permits the flow of liquid through the septum via the hollow needle. The connectors are locked into place by bringing the male connector as far forward as possible, and then rotating the male connector such that the extended knobs move past the restriction in the cutout and click (lock) into place. Quick release is obtained by rotating the male connector in the opposite direction and pulling the male connector straight out relative to the female connector. When the male and female connectors are separated, the needle in the female connector is withdrawn from the self-sealing resilient septum attached to the reduced diameter second end of the male connector.

The male connector of the IV quick-connect/disconnect safety assembly may be fabricated as the termination of the branch of a Y-site on an extension set. This makes it possible to add a second source of IV fluid via a bag, bottle, or syringe. Where a piggyback or secondary extension set is utilized, a female connector for mating with the male Y terminator is provided, as summarized above. However, where a syringe is utilized the syringe is preferably coupled with its male luer-lock or luer-slip to the female luer of the above-summarized female connector. That assembly is then connected to the male connector which completes the assembly and establishes the flow path in the IV administration system. When the syringe is removed after injection, the female connector stays attached to the syringe and reduces the probability of accidental needle-sticks.

Additional objects and advantages of the invention will become apparent to those skilled in the art upon reference to the detailed description in conjunction with the accompanying drawings.

BRIEF DESCRIPTION OF THE DRAWINGS

FIG. 6a–6c illustrate the location and relationship of the IV connector assembly of the invention relative to the other components that make up possible IV administration systems.

DETAILED DESCRIPTION OF THE INVENTION

Figure 1:
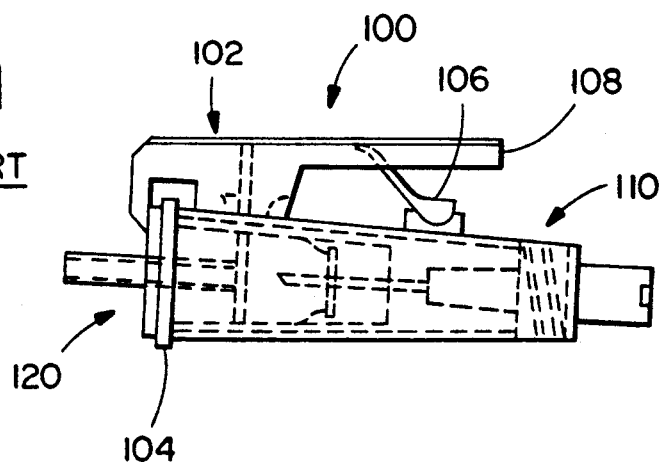
FIG. 1 is a perspective of a two piece prior art connector utilizing a spring loaded lever for locking together a male and a female connector.
Figure 2:
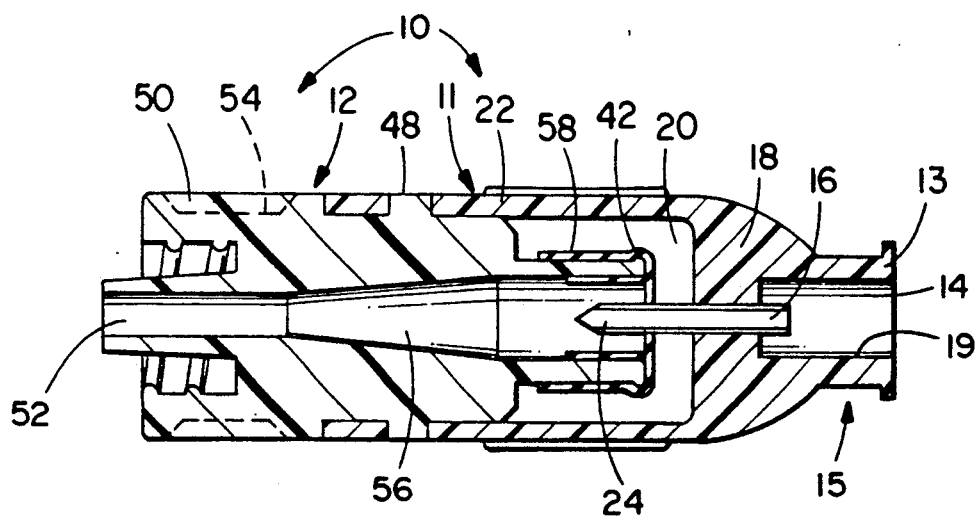
FIG. 2 is a cross section through the IV quick-connect/disconnect safety assembly invention.
Figure 3:
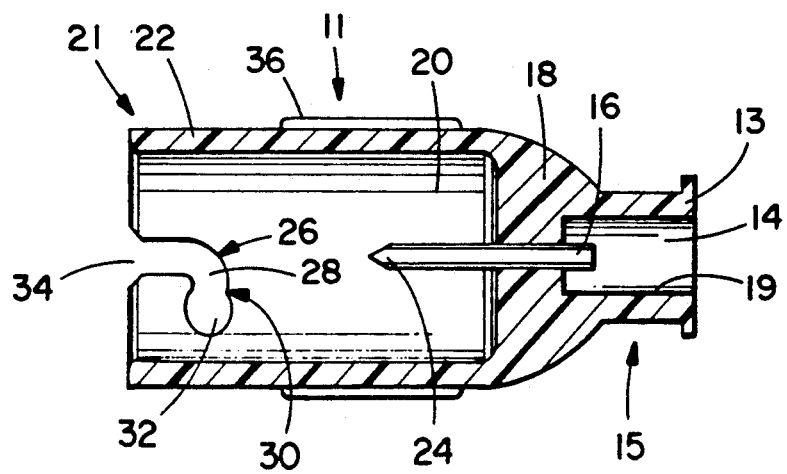
FIG. 3 is a cross section through the female connector of the IV quick-connect/disconnect safety assembly invention.

As seen in FIG. 2, the IV quick-connect/disconnect safety assembly 10 of the invention comprises a female connector 11 and male connector 12. The female connector 11, as shown in FIG. 3, has a reduced end 15 and an enlarged end 21 separated by a dividing wall 18. The reduced end 15 forms a female luer lock with a female luer 19 and a tab 13. The enlarged end 21 is defined by a cylindrical wall 22 which surrounds a cylindrical receiving area 20.

A hollow needle 16 is insert molded or bonded in the dividing wall 18 so that the pointed end of the needle 24 is located in the receiving cylinder, the hollow needle forming a passageway between the tapered bore 14 of the female luer lock and the receiving cylinder. The receiving cylinder wall 22 has one or more bayonet type cutouts 28 having a first section which is parallel to the long axis of the female connector and a second section which is perpendicular to and a continuation of the first section in the perpendicular direction. Entrance to the cutout is at the open end of the receiving cylinder, and the cutout has a restriction 30 which reduces the entry way into the circular area 32. The female connector is molded from plastic or other acceptable materials and has a plurality of integral tapered, smooth, plastic ribs 36 on the exterior surface of the cylindrical wall 22 running in the direction of the longitudinal axis of the female connector which serve the purpose of providing finger grips.

Figure 4:
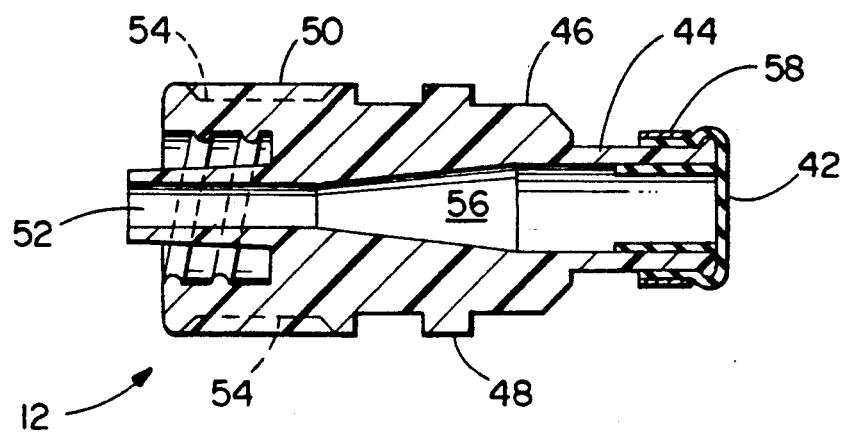
FIG. 4 is a cross section through the male connector of the IV quick-connect/disconnect safety assembly invention.

The male connector 12, shown in FIG. 4, has a male luer lock 52 on a first end 50, a middle portion 46 of slightly reduced outer diameter with one or more outwardly extending rounded knobs 48, and a second end 44 of further reduced outer diameter. First end 50 is preferably ribbed by cutting into the exterior cylindrical surface as shown by dashed lines 54 to form a finger grip. Second end 44 is covered by a resilient septum 42 fitted to and preferably covering at least a portion of both the interior and exterior wall surface of second end 44. The resilient septum is held in place by a thin plastic shrink band 58 or other acceptable means which surrounds the outer surface of the septum on the second end 44. The first end 50, the middle portion 46, and the second end 44 of the male connector 12 encompass a bore 56 which preferably enlarges as it proceeds from the first end 50 towards the second end 44 of the male connector 12.

In connecting the male and female connectors to make up the invention assembly as shown in FIG. 2, the male connector is positioned so that the reduced diameter second end 44 of the male connector is introduced into the receiving chamber 20 of the female connector 11 with the rounded knobs 48 of the male connector being in position at the openings 34 of the bayonet cutouts 28 (see FIG. 3) in the female connector. The male connector is pushed forward as far as it will go until the knobs come in contact with the cutout surface shown as 26. The male connector is then rotated so that the knobs go past the restriction 30 in the radius wall and come to rest in the cutout pockets 32 shown in FIG. 3. The cutout pockets 32 in conjunction with the restriction 30 apply sufficient force to the knobs to securely hold the assembly together. When the male and female connectors are locked together, a distinct audible click is heard signaling to the person assembling the connectors that the connection is secure.

When the reduced diameter 44 of the male connector 12 is pushed forward as described above, the needle 16 of the female connector 11 pierces the septum 42 and permits fluid to flow from chamber 14 shown in FIGS. 2 and 3 through the needle 16 and into bore 56. When the male and female connectors are mated, the knobs 48 of the male connector are substantially flush with the cylindrical wall 22 of the receiving cylinder which is part of the female connector. As a result, the outside surfaces of the male and female connector when joined present a smooth surface; there are no projections outward from the body of the assembled connector.

When the male and female connectors are to be disconnected, the male connector 12 is rotated so that the knobs 48 move past the restriction 30 in the bayonet cutouts in cylindrical wall 22 of the female connector 11. Then the male connector 12 is pulled straight back so that the knobs pass down the longitudinal part of the cutouts to the entry way 34. As the male connector is removed, the needle is withdrawn from the resilient self-sealing septum 42 which immediately seals and cuts off fluid flow. The self-sealing septum 42 also keeps out bacteria, dirt, dust and other contaminates from the patient side of the IV administration system. When disconnected, the needle 16 in the female connector 11 is shielded by the receiving cylinder wall 22 so that inadvertent needlesticks are reduced to a minimum. This is an important safety feature.

In the preferred embodiment, the middle portion 46 of the male connector 12 is sized to loosely contact the receiving cylinder walls 22 of the female connector when mating, thereby serving the added function of centering the male connector so that the needle point 24 is centered when it pierces the septum 42.

Figure 5:
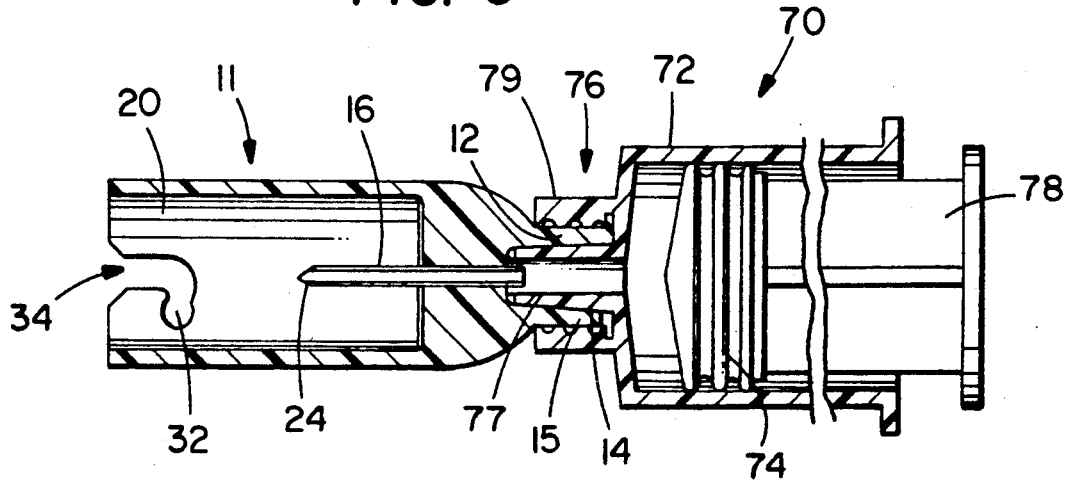
FIG. 5 is a cross section through the female connector of the IV quick-connect/disconnect safety assembly invention showing its use with a syringe having a luer-lock on its distal end.

Use of the female connector 11 in conjunction with a syringe 70 for introducing medicament or other fluid into an IV system is illustrated by FIG. 5. As previously described, the female connector 11 has a female luer-lock or luer-slip on its reduced end 15. A syringe 70 with a cylindrical barrel formed by wall 72 has a reduced end 76 forming either a male luer-lock or luer-slip (the luer-lock being shown). The male luer-slip 77 of the luer-lock 79 is inserted into the tapered bore 14 formed by the female luer-lock or luer-slip of the female connector 11 by screwing or pushing the two together. When the female connector 11 and the syringe 70 are assembled in this manner, fluid in the syringe 70 may be expelled from the syringe by plunger 78, thereby forcing the fluid through the hollow needle 16 and into the IV administration line. After injection, the syringe 70 with the female connector 11 attached thereto is removed from the resilient septum which then seals. The needle 16, however, which could have been infected in the injection process due to migratory bacteria or blood contamination, is not exposed as it is shielded by the receiving cylinder wall 22 of the female connector 11. The use of the syringe 70 and female connector 11 combination is thus attractive because accidental needlesticks are substantially reduced.

FIG. 6a shows the relationship of the assembled connector 10 in a typical IV administration system. On the medication side of the quick-connect/disconnect assembly 10, the IV solution 86 is connected via tubing 84 which has a male luer 80-1 on its end. The male luer is inserted into a female luer-lock of the female connector 11 of the IV quick-connect/disconnect safety assembly 10 of the invention. On the patient side of the quick-connect/disconnect assembly 10, an extension tube with two ends has a first end with a female luer 82-1 which is inserted into a male luer-lock 50 of the IV quick-connect/disconnect safety assembly male connector 12. A second end of the extension tube has a male luer 80-2 attached to it which in turn mates with a female luer 82-2 on the end of a catheter, winged needle, or other IV device 90. To permit fluid flow of medication to the patient, the female connector 11 and the male connector 12 which make up the complete quick-connect/disconnect assembly 10 are mated.

FIG. 6b shows a similar type IV administration system to that of FIG. 6a except that a Y-site connector 92 is placed in conjunction with an extension line group (female luer 82-1, line 84, and male luer 80-2) between the IV solution 86-1 and the assembled quick-connect/disconnect device 10 of the invention. The Y-site connector 92 allows other medicaments and fluids to be administered through the septum fitted male connection (PRN) 97 shown as the termination of the branch of the Y-site connector 92, such as by utilizing the female connector 11 of the invention in conjunction with male luer 80-3 and bag or bottle 86-2. Regardless of whether the PRN device 97 shown in FIG. 6b is the male connector 12 of the IV quick-connect/disconnect safety assembly of the invention, or a connector of another manufacturer, the female connector 11 and syringe 70 assembly described above with reference to FIG. 5 can be used as a safety combination for injecting medication into the IV administration line (as more particularly seen in FIG. 6c). In addition, if the PRN device 97 is indeed the male connector 12 of the quick-connect/disconnect assembly 10 of the invention, a female connector 11 attached to another fluid source (not shown) could be utilized in the manner previously described to establish a second quick-connect/disconnect fluid path.

FIG. 6c shows that is it possible to introduce more than one Y-site connector 92 at a time into the IV system. In fact, it will be appreciated by those skilled in the art that the components shown in FIGS. 6a-6c can be mixed and matched in several ways at the convenience of the practitioner. In addition, groups of components can be manufactured or assembled as a group to perform standard functions; e.g. female luer 82, line 84 and male luer 80 forming an extension line; bag or bottle 86, line 84 and male luer 80 forming a fluid source; catheter or winged needle element 90, line 84, and female luer 82 forming a catheter, winged needle, or other IV device connection group.

There have been described and illustrated herein a quick-connect/disconnect device for an IV administration line system. While particular embodiments of the invention have been described, it is not intended that the invention be limited thereby, as it is intended that the invention be as broad in scope as the art will allow. Thus, it will be appreciated by those skilled in the art that the term "IV fluid" is intended to be understood in a broad sense to include blood or blood products, and the term "administration" is used in its broad sense to include the dispensing or collection of the IV fluid. Also, it will be understood that while the male connector was described as having three sections of decreasing sizes, the middle section can be of the same diameter as the section having the septum thereon, provided the knobs extend far enough to run in and lock in the bayonet cutouts of the female connector. Further, while the female connector was illustrated as preferably having a female luer-lock on one end, and the male connector was illustrated as preferably having a male luer-lock on one end, it will be appreciated that, although not preferred, simple luer-slips could be utilized in lieu of luer-locks. Also, while the central bore in the male connector was described as increasing in size as it extended from the male luer-lock end to the septum end, it will be appreciated that the central bore could be of substantially constant diameter, or of changing diameters which do not increase in size as described. Further yet, it should be appreciated that while the female connector was described as having a hollow needle insert molded or bonded into a wall dividing the sections of the female connector, the needle could be or formed in different manners. For example, the needle could be a plastic needle or piercing device formed as part of the molding process as an integral part of the female connector. Therefore, it will be appreciated by those skilled in the art that yet other modifications could be made to the provided invention without deviating from its spirit and scope as so claimed.

I claim:

1. A two piece fluid line connection assembly for permitting the coupling and uncoupling of an influent supply line terminating in a first male luer and an effluent supply line starting with a first female luer, the assembly comprising:

a) a female connector having first and second hollow portions, a dividing wall separating said first and second hollow portions, and a hollow needle having a first sharp end, said first hollow portion having a first substantially cylindrical wall forming a receiving chamber with a first substantially open end, said first substantially cylindrical wall having at least one bayonet cutout therethrough, said second hollow portion having a second substantially cylindrical wall with an inside surface forming a second female luer for mating with said first male luer of said influent supply line, and an outside surface of reduced outer diameter relative to the outer diameter of most of said first substantially cylindrical wall, and said hollow needle forming a passageway through said dividing wall and connecting said receiving chamber and said second female luer, with said first sharp end of said hollow needle extending into said receiving chamber, and with said sharp end of said needle being substantially recessed in said receiving chamber relative to said first substantially open end of said receiving chamber so as to prevent contact of a human finger therewith, thereby reducing needlestick injuries;

b) a male connector with a hollow first end cylindrical portion having a first opening, a hollow middle body cylindrical portion, a hollow second end cylindrical portion with a second male luer for mating with said first female luer of said effluent supply line extending therefrom, and a resilient septum, said hollow first end cylindrical portion being fitted with said resilient septum at said first opening, and said hollow first end cylindrical portion and said hollow middle body cylindrical portion being of reduced outer diameters relative to the inner diameter of said receiving chamber of said female connector, said hollow middle body cylindrical portion having at least one outwardly extending bayonet knob, the outer diameter of said extending bayonet knob being of substantially the identical outer diameter of the outer diameter of said receiving chamber, and the outer diameter of said hollow second end cylindrical portion is substantially identical to the outer diameter of said receiving chamber, wherein said bayonet cutout includes a locking section, and said bayonet cutout and said outwardly extending knobs are dimensioned such that said outwardly extending knobs are received in said bayonet cutout and can lock in said locking section, and the axial distance between the locking section of said bayonet cutout and the sharp end of said needle along a longitudinal axis of said female connector is smaller than the axial distance between said septum and said outwardly extending knobs along a longitudinal axis of said male connector such that when said said female connector and male connector are mated, said sharp end of said needle pierces said septum, and when said female connector and male connector are mated, a substantially smooth, substantially continuous outer cylindrical surface is presented comprised of said outer surface of said hollow second end cylindrical portion of said male connector and said first substantially cylindrical wall of said female connector, with said outwardly extending knobs of said male connector in said bayonet cutout of said female connector, wherein said female connector comprises a first piece of said two piece fluid line connection assembly, and said male connector comprises a second integrally formed piece of said two piece fluid line connection assembly.

2. A fluid line connection assembly according to claim 1, wherein:

said dividing wall of said female connector has a smooth outer surface which tapers from the outer diameter of said receiving chamber to the outer diameter of said second hollow portion of said female connector.

3. A fluid line connection assembly according to claim 2, wherein:

said second female luer of said female connector comprises a female luer-lock.

4. A fluid line connection assembly according to claim 2, wherein:

said second male luer of said male connector comprises a male luer-lock.

5. A fluid line connection assembly according to claim 3, wherein:

said second male luer of said male connector comprises a male luer-lock.

6. A fluid line connection assembly according to claim 1, wherein said second female luer of said female connector comprises a female luer-lock, and said second male luer of said male connector comprises a male luer-lock.

7. A fluid line connection assembly according to claim 1, further comprising:

a plastic shrink band for holding said resilient septum in place in and around said first opening of said male connector.

8. A fluid line connection assembly according to claim 5, further comprising:

a plastic shrink band for holding said resilient septum in place in and around said first opening of said male connector.

9. A fluid line connection assembly according to claim 7, wherein:

said resilient septum is a self-sealing resilient septum.

10. A fluid line connection assembly according to claim 1, wherein:

said male connector and female connector are molded from plastic.

11. A fluid line connector assembly according to claim 10, wherein:

said hollow needle with said sharp first end is plastic and is formed simultaneously with said female connector in a molding process.

12. A fluid line connector assembly according to claim 1, wherein:

said male connector and said female connector are mlded from plastic, said hollow second end cylindrical portion of said male connector is molded with indentations in its outer surface as finger grip means for said male connector, and said first substantially cylindrical wall of said female connector is molded with longitudinally extending tapered ribs on its outer surface as finger grip means for said female connector.

13. A fluid line connector assembly according to claim 5, wherein:

said male connector and said female connector are molded from plastic, said hollow second end cylindrical portion of said male connector is molded with indentations in its outer surface as finger grip means for said male connector, and said first substantially cylindrical wall of said female connector is molded with longitudinally extending tapered ribs on its outer surface as finger grip means for said female connector.

* * * * *